United States Patent [19]

Wahlquist

[11] Patent Number: 4,671,943
[45] Date of Patent: Jun. 9, 1987

[54] STERILIZATION AND STORAGE CONTAINER

[75] Inventor: Joseph D. Wahlquist, Woodstock, Ga.

[73] Assignee: Kimberly-Clark Corporation, Neenah, Wis.

[21] Appl. No.: 605,039

[22] Filed: Apr. 30, 1984

[51] Int. Cl.⁴ .............................................. A61L 2/20
[52] U.S. Cl. .................. 422/300; 422/311; 206/363; 206/439; 206/484.1; 220/324; 220/344; 220/371; 220/374; 55/501; 55/511; 55/529
[58] Field of Search ............ 422/26, 28, 297, 300, 422/311; 55/279, 501, 511, 528, 529; 206/363, 439, 484.1; 220/324, 344, 371, 374

[56] References Cited

U.S. PATENT DOCUMENTS

| | | | |
|---|---|---|---|
| 1,939,715 | 12/1933 | Meitzler | 422/300 |
| 2,384,398 | 9/1945 | Raven | 422/300 |
| 3,017,698 | 1/1962 | Hambrecht et al. | 55/501 X |
| 3,577,712 | 5/1971 | Ballennie et al. | 55/501 |
| 3,793,692 | 2/1974 | Tate et al. | 55/501 X |
| 3,820,308 | 6/1974 | Oruki | 55/279 |
| 4,041,203 | 8/1977 | Brock et al. | 428/302 X |
| 4,105,407 | 8/1978 | Sanderson | 422/26 |
| 4,247,517 | 1/1981 | Sanderson et al. | 422/26 |
| 4,358,908 | 11/1982 | Song | 220/371 X |
| 4,372,921 | 2/1983 | Sanderson et al. | 422/300 |

FOREIGN PATENT DOCUMENTS

| | | | |
|---|---|---|---|
| 2207339 | 9/1973 | Fed. Rep. of Germany | 422/300 |
| 2839219 | 3/1980 | Fed. Rep. of Germany | 206/439 |
| 2375809 | 7/1978 | France | 422/300 |

Primary Examiner—David L. Lacey
Attorney, Agent, or Firm—Patrick C. Wilson

[57] ABSTRACT

A container for sterilizing, and storing and presenting surgical instruments and materials in a sterilized condition has a container base member with a cover and bottom and side apertures for passage of a sterilizing agent; a sealing gasket between the container cover and the base member provides a seal and a tortuous path constituting a probability filter is provided exteriorly of the seal; a removable tray for instruments to be sterilized is carried within the container; a removable filter element commensurate in shape to the container base member is located intermediate the removable tray and the bottom of the container base member; the filter element may be of a soft formed element or may have a frame and is located with a portion extending outwardly between the base member and cover past the sealing gasket; the filter element provides a filter path permitting passage of sterilizing agent received through the bottom and side apertures into the container while the filter element inside the container and the tortuous path constituting a probability filter outside the container present a barrier to the passage of microorganisms to instruments in the tray after being sterilized.

18 Claims, 17 Drawing Figures

STERILIZATION AND STORAGE CONTAINER

TECHNICAL FIELD

The present invention relates to an improved container for sterilizing, and storing and presenting surgical instruments and materials in a sterile condition. More particularly, the present invention relates to a sterilization and storage container which includes a filter element and a tortuous path arrangement providing a probability filter, the filter element and the probability filter presenting a barrier to entry of microorganisms which would contaminate instruments after being sterilized.

BACKGROUND ART

Methods employed to sterilize articles generally, and surgical instruments and materials particularly, have included the use of heat, radiation, ultraviolet light, a sterilizing agent, such as a gaseous substance, and combinations of the foregoing. Particularly when applied to surgical instruments, materials or prosthetic devices, the article is placed within a container or package which is heated and/or treated with a sterilizing gas. Heat alone has been shown to be less effective as a method of sterilization than the use of a sterilizing gas alone or the combination of a sterilizing gas with heat.

To be effective as a container or package for sterilizing such articles as surgical instruments and related materials, the container or package should, after closing or sealing, permit ingress and egress of a sterilizing agent but bar entry of microorganisms which could contaminate the materials stored within. To be suitable, the container or package must also maintain the sterility of the articles within until such time as the container or package is opened and the articles removed for use.

One of the more commonly used methods for sterilizing surgical instruments and materials still used today involves wrapping the articles with pieces of woven fabric, such as towels or sheets of muslin or the like or with pieces of disposable nonwoven fabric, taping the wrapped package shut, and placing the package in a sterilizing autoclave. Sterilizing steam, which enters the autoclave chamber, penetrates the porous fabric of the package and contacts the articles contained within. Some autoclaves provide for removal of air before introduction of steam and/or the removal of moisture after autoclaving by means of a vacuum drying cycle. With most of such devices, atmospheric pressure is restored within the autoclave by admitting room air prior to removal of the package placed therein. This permits non-sterile air and particles to be drawn into the autoclave, possibly penetrating the porous fabrics, along with lint from the towels, as air is drawn into the center of the package. Scientific studies have indicated that approximately 30 percent of packages prepared with sheets or towels are contaminated by microorganisms at the time of use. This method is also less than satisfactory when the package contents are not used immediately after removal from the autoclave since the potential for contamination increases with the period of time passing after sterilization. Thus, if the sterilized articles are not used shortly after removal from the autoclave, even though the package remains unopened, the articles should be resterilized. When using this method of sterilization, it has been estimated that as much as two-thirds of sterilization work in many hospitals results from resterilization of items not used within the accepted shelf life of the package. The labor and time of personnel involved in such resterilization is wasted, resulting in higher costs with no benefit.

The loss or damage of expensive instruments is another consequence commonly resulting from use of this method. Frequently the muslin wrapper is spread out on a table in an operating room and the contaiminated instruments are placed thereon after use. Subsequently the muslin may be gathered up and disposed of with the instruments inside and/or tossed into a laundry basket, damaging the instruments thereby.

Labor and time of personnel are required to wrap instruments for sterilization which contribute to the inefficiency of the foregoing method. Recognition of this inefficiency has led to the development of a variety of reusable sterilization containers and methods employing such containers which may be used in conjunction with sterilizing gases. These reusable containers range from relatively simple devices, such as a closed container having apertures therein or a sieve placed in the bottom of the container for entry of a sterilizing agent, to complex devices, such as containers provided with elaborate mechanisms for closing the cover of the device after a sterilizing gas has had sufficient time to enter the container. Other containers, intermediate in complexity between the aforementioned devices, are those sterilization containers having apertures passing from an outer surface to an inner surface of the container and provided with a porous material covering one of the apertured surfaces. The porous material is selected to permit passage of air and other gases but to be impervious to the passage of microorganisms. All of such devices are intended to provide ingress and egress of air or a sterilizing gas during the sterilization procedure but to exclude contaminants during and subsequent to the sterilization procedure. There are certain shortcomings associated with such devices, however. In some instances, a problem arises from the nature of the materials used for the bacterial barrier and the air/sterilant gas pathway. That is, in some instances, the openings or pores of the materials are sufficiently large to permit entry of microorganisms. In other instances, the material is not sufficiently porous to permit passage of sterilizing gas. In the latter situation, sterilization is not properly accomplished and in the former situation, although sterilization is complete, the contents of the container are subsequently contaminated.

Even when the barrier material is appropriately selected, many of the above-described devices which employ such a barrier still fail to provide adequate sterilization of the articles contained within the device or, more frequently, fail to maintain the articles in an asceptic condition. In many situations, the barrier material is pliant or fragile and may be easily snagged or torn, thereby allowing access of microorganisms to the interior of the container. In other situations, the pliant material, serving as the microorganism barrier/gas admitting filter, must be stretched and/or properly aligned and clamped in place before the sterilization procedure is begun. If this is not carefully done, an opening may exist in those regions of the container where the material is intended to be effectively secured or clamped.

DISCLOSURE OF THE INVENTION

The present invention has as its principal object to provide a lightweight combination sterilization, storage and delivery device for surgical instruments which can be rapidly assembled and disassembled and which will assure maintenance of an aseptic condition of the interior of the device and the contents thereof after a sterilization procedure.

A further object is to provide such a device having a removable transparent cover to allow trained personnel to see the instruments and also allow a sterile nurse access to the instruments within the container, thus avoiding contact by the nurse with an outside surface of the storage device, which may be contaminated, either in visually inspecting the interior contents of the container or in accessing its contents.

Another object is to provide a filter element for such a device.

A combination sterilization and storage device according to the present invention includes a container base member having apertures in the bottom and sides and a container cover on the base member. A filter element is placed within the base member lying over the bottom and side apertures, the filter element being substantially commensurate in shape to the container base member. A tray or basket containing the items to be sterilized is placed within the base member above the filter element. Provision is made for combined hinging and clamping the cover to the base member to provide an interior chamber. The filter element, which is preferably disposable, includes a filter sheet which allows passage of air and sterilizing medium while also serving as a microorganism-stopping barrier. The filter element either includes a rigid frame member around the periphery of the filter sheet or the filter sheet may be shaped as a three dimensional element without a rigid frame member around the periphery. In either case, the filter element has the same shape as the inside of the container base, nests therein and may be exactly located when placed in position. A gasket seal is provided between the container cover and the base member around the periphery of the filter element. This assures proper sealing of the filter element so that the microorganism barrier presented by the filter sheet is effective subsequent to sterilization to block a direct path through which sterilizing agent is admitted during sterilization, defining thereby, after sterilization, an aseptic region within the interior chamber of the container above the filter element in which the basket is located containing the items to be sterilized. This overcomes a problem of some prior art sterilizing devices in which filter elements, cut from pliant material, rather than being shaped to the configuration of the container, are simply folded into position and, because of gaps due to the absense of a close fit with the sealing arrangement, do not effectively provide a microorganism barrier after sterilization. To further assure the effectiveness of the filter sheet in providing a barrier to the entry of microorganisms after sterilization, the outside walls of the container are constructed to provide a tortuous path exterior of the seal, constituting a probability filter and serving as a barrier to passage of microorganism from outside the container to the seal. With this construction the sole access for microorganisms from outside the container to the interior chamber is either through the direct path and filter sheet or the tortuous path probability filter and seal, both of which are effectively blocked.

BRIEF DESCRIPTION OF DRAWINGS

FIG. 3b is a fragmentary plan view of the container base member shown in FIG. 3a;

FIG. 10 illustrates in a perspective view the embodiment of the filter element for the sterilization container shown in FIG. 3a;

BEST MODES FOR CARRYING OUT THE INVENTION

Figure 1:
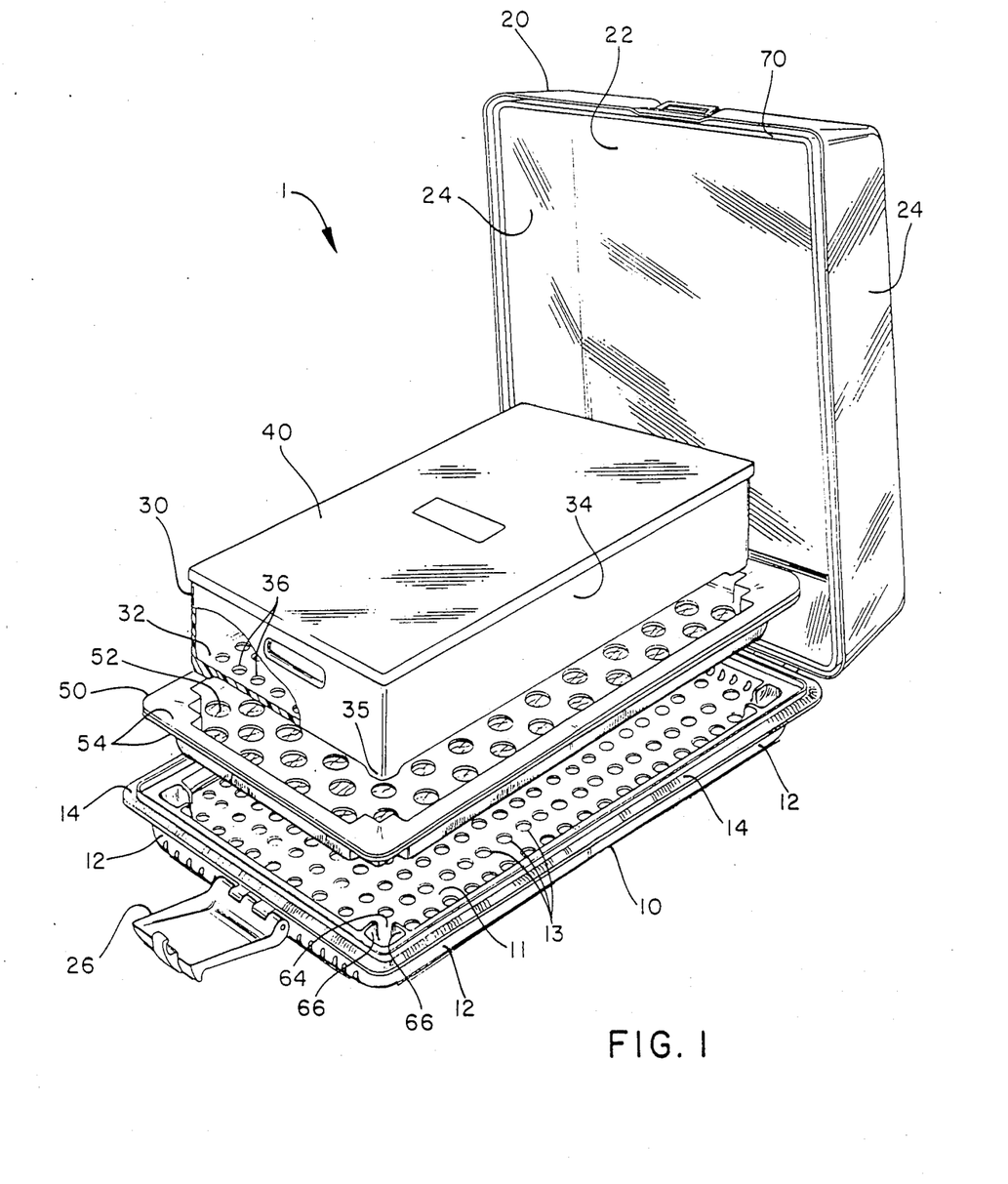
FIG. 1 is a partially exploded and partially cut away view, in perspective, of an embodiment of the sterilization and storage container according to the present invention in an open position.
Figure 2:
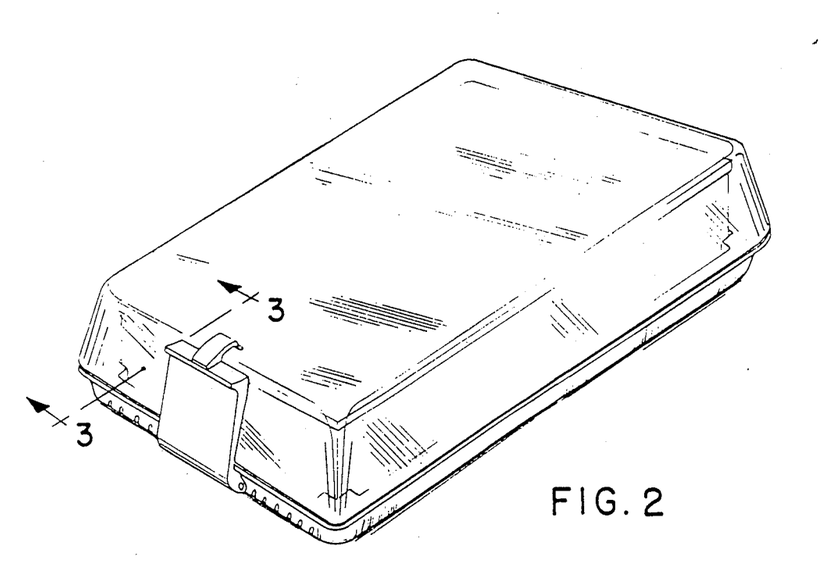
FIG. 2 is a perspective view of an embodiment of the present invention in a closed position.

Turning first to FIG. 1, there is shown an embodiment of the sterilization and storage container 1 according to the present invention. The container includes a container base member 10 having a bottom 11 and side wall or wall portions 12. Although the sterilization and storage container of the present invention may have any general configuration, i.e., with a round, elliptical, square, or rectangular top and bottom, with corresponding side wall portions, the preferred configuration is as shown in FIGS. 1 and 2, a rectangular cover and base member. To facilitate run-off of condensed water when steam is employed as the sterilizing agent, the container base member side walls 12 may be inclined outwardly toward its open, upper end, as is shown more clearly in FIG. 3. To permit ingress and egress of air and sterilizing fluid into container 1, apertures 13 are provided in the bottom 11 and side walls 12. To avoid collection of condensation and facilitate drainage of water from within the container when steam is used as the sterilant, the bottom 11 of the base member is arranged with an incline, preferably declining from an intermediate or central portion toward its extremities, that is, the wall portions 12. The container base member is also provided with a peripheral, laterally directed, rim or flange 14 contiguous to the open, upper portion of the side wall portion.

A hinge 18 (illustrated in greater detail in FIGS. 11 and 12) is provided to rotatably and detachably secure and align the container cover 20 to the container base member 10.

Figure 3:
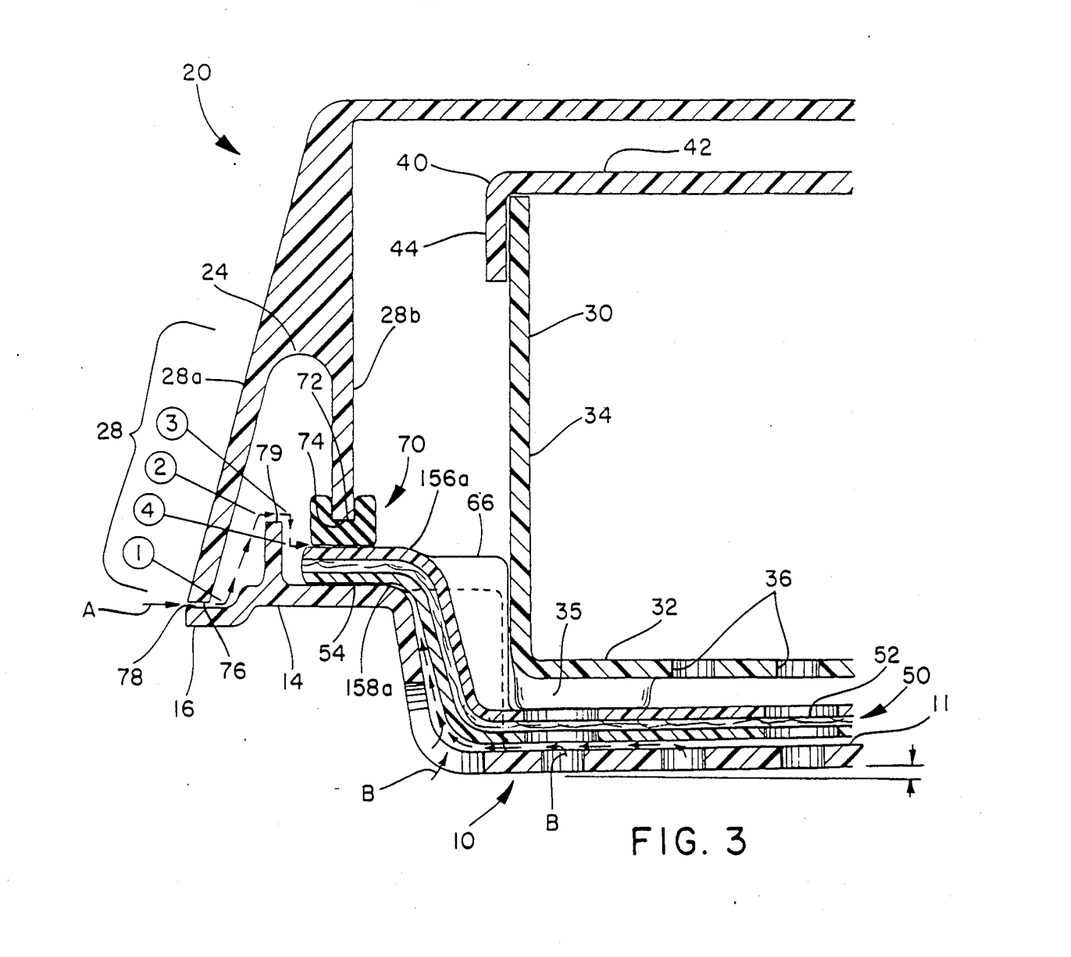
FIG. 3 is a partial sectional view of an embodiment of the sterilization container, filter element and instrument tray according to the present invention taken along section line 3—3 of FIG. 2.

Container cover 20, shown in FIGS. 1 to 3, includes a top 22, which is preferably planar, and a side wall or wall portions 24. To facilitate run-off of condensed water when steam is employed as the sterilizing medium, and for other purposes discussed below, the cover side wall portions 24 decline outwardly toward the open end of container top 20. The container top may also be provided with recesses or protrusions (not illustrated) in the outer surface of the container top side walls to permit grasping of the container top.

Figure 13:
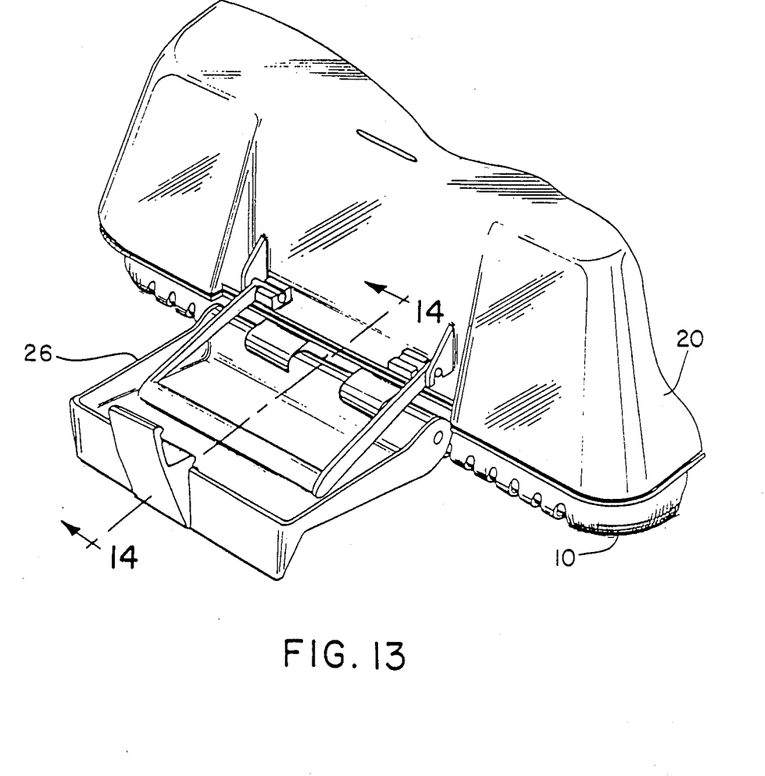
FIG. 13 depicts in perspective a locking mechanism employed in the present invention to secure the sterilization container cover to the container base member.
Figure 14:
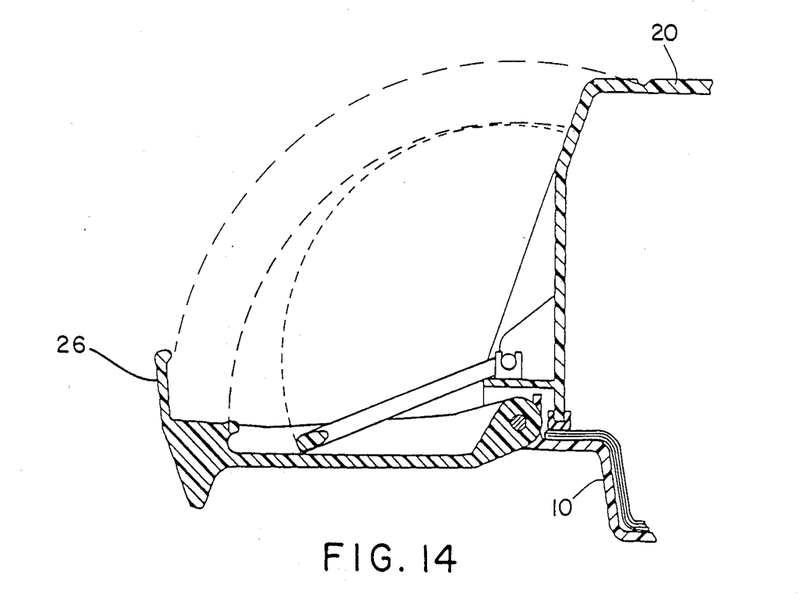
FIG. 14 illustrates in section the locking mechanism and portions of the container cover, base member and filter element of the embodiment shown in FIG. 13 taken along line 14—14.

As shown in greater detail in FIGS. 13 and 14, a clamping or locking means 26, such as a bale pivotally secured to the container cover or, preferably, to the container base member, permits secure closure of the container 1 to prevent accidental opening and accidental contamination.

The outwardly sloping configuration of the wall portion 24 of container cover 20 provides additional benefits besides permitting drain-off of condensed water. Once the clamping mechanism is released and the hinged cover is pivoted upwards, any contaminants falling from the hand lifting the cover or the wall portion itself would be deflected by the sloping configuration of the wall, rather than dropping directly into the sterile container base member.

The base member 10 and cover 20 together define an interior chamber in which a removable receptacle 30 is provided in the form of a tray or basket for holding the articles to be sterilized. The tray 30 includes a tray bottom 32 and tray wall or wall portions 34. Preferably, the tray bottom 32 is provided with apertures 36 passing therethrough. The apertures 36, like those in the container base member, are provided for ingress and egress of sterilizing agent and, when steam is employed as the sterilant, condensed water. The apertures 36 are arranged so that they do not line up with the apertures in the base member, thus providing better support for small instruments in the tray. In addition, the path into the tray from the outside is tortuous to assist in blocking entry of bacteria. The tray walls 34 may be disposed vertically or substantially perpendicular to the container bottom 11, as shown in FIG. 3, or may incline or flare outwardly from the bottom toward the open, upper end of the tray. The tray is also preferably provided with a tray cover 40 having a top 42 and substantially downward depending side wall or wall portions 44 (FIG. 3). As shown in FIG. 3, to permit sterilizing agent to contact the top edges of the walls 34 of the tray when a tray cover is employed, bumps may be provided on the top edges of the tray as a means for maintaining a clearance space between the under surface of the tray cover and the top edges of the tray.

The tray 30 may be provided with instrument securing means mounted within the tray, preferably on its bottom. Such securing means may take the form of clamps or simply pins or rods inserted permanently or, preferably, removably, within apertures 36.

Feet 35 may be provided on the bottom of the tray to support and maintain the tray in a spaced relation from a surface on which it rests, such as the filter element 50, discussed below.

Materials which are suitable for use for the container cover, base member, tray and tray cover should be able to withstand both reduced pressures and temperatures commonly employed for heat or steam sterilization and remain inert toward sterilizing agents such as ethylene oxide. Sheet steel, aluminum, thermosetting polymers and thermoplastic polymers which are stable at elevated temperatures are suitable. In many situations it is desirable to be able to observe the contents of the container or the tray, as when a time/temperature indicator is used to assure the sufficiency of sterilization. In such instances, transparent plastics which are stable at elevated temperatures may be used to form the container base member, tray and their corresponding covers or merely the covers. Suitable transparent heat resistant plastics include polycarbonates but are preferably polysulfones, polyethersulfones and polyetherimides.

In carrying out the invention, a disposable, removable liner or filter element 50 is placed within the interior chamber defined by the container base member 10 and the container cover 20, lying intermediate the container base member bottom 11 and the tray bottom 32. The term "filter element" is employed herein to indicate a structure which permits the passage of air or a sterilant, such as a sterilizing agent as, for example, steam, ethylene oxide, mixtures of ethylene oxide and freon, and the like, which structure is also capable of filtering out or retaining particulate matter and microorganisms, such as bacteria, viruses, and the like.

Figures 4, 5, 6:
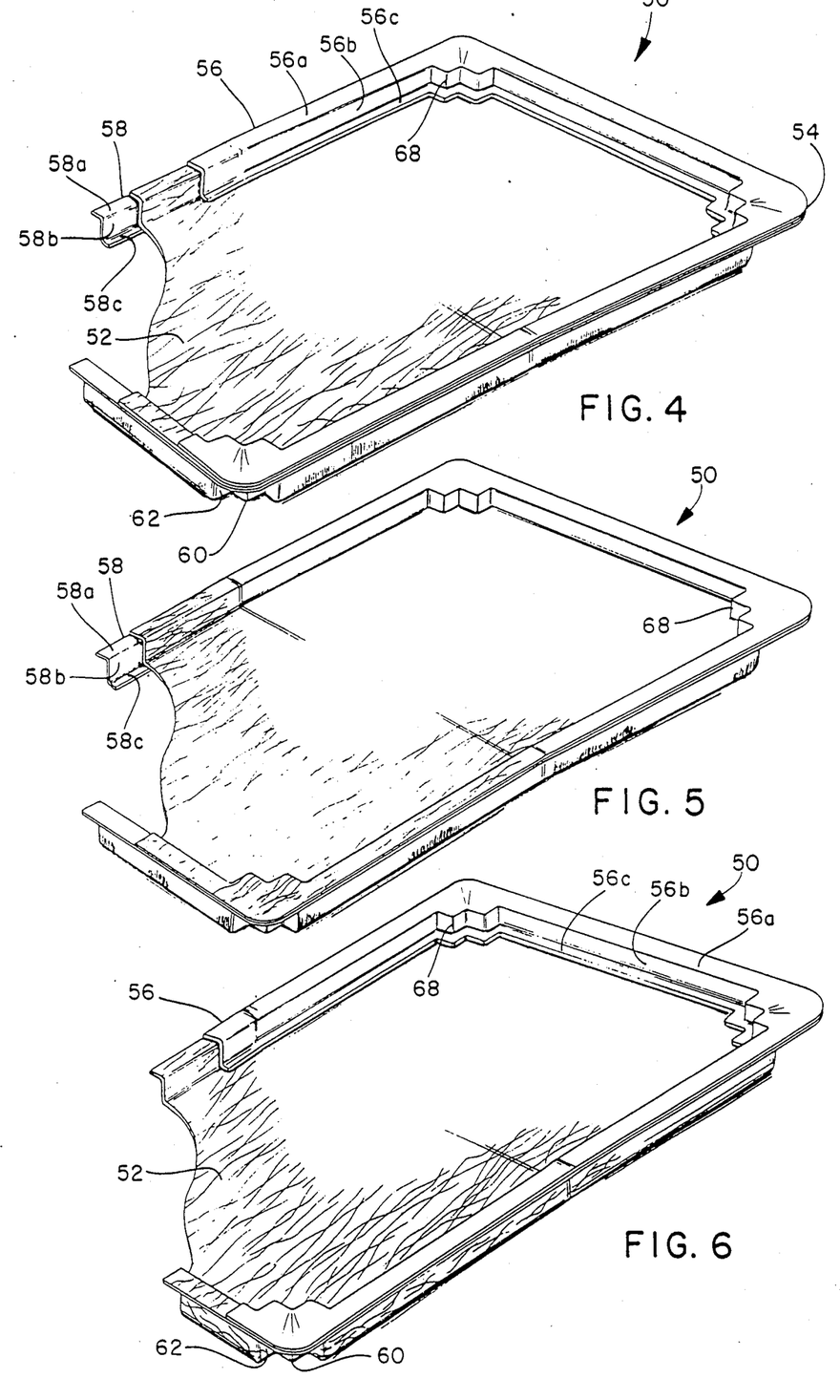
Figure 4 illustrates in perspective an embodiment of the filter element according to the present invention.
FIG. 5 shows a perspective view of another embodiment of the filter element according to the present invention.
FIG. 6 depicts, in perspective, still another embodiment of the filter element according to the present invention.
Figure 9:
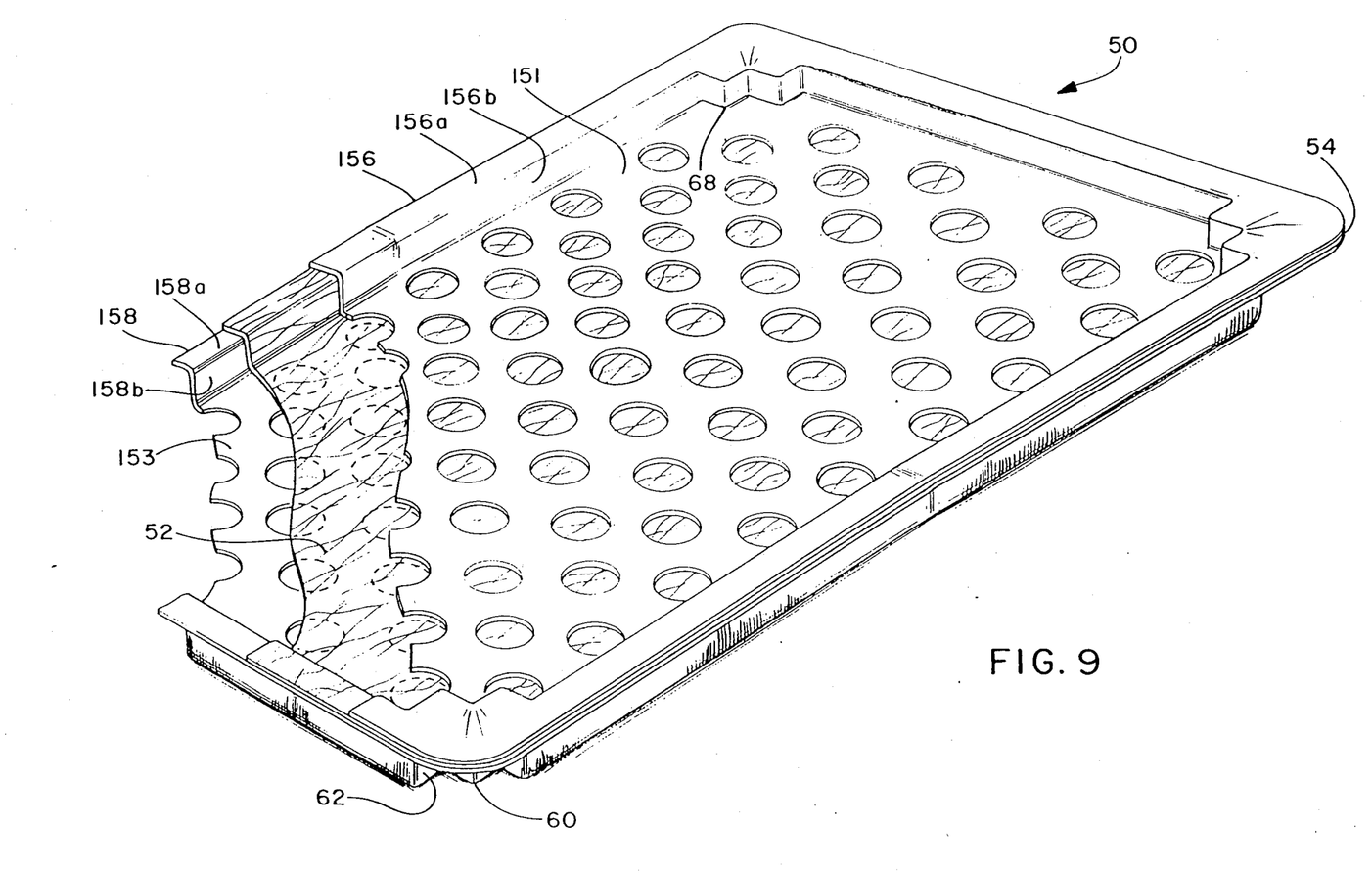
FIG. 9 illustrates in a perspective view a preferred embodiment of the filter element according to the present invention.

FIGS. 1 and 3 to 10 illustrate various embodiments of filter elements according to the present invention. In its preferred form, the filter element 50 includes a filter sheet 52 secured to a frame member 54 providing a rim portion. Depending upon the materials selected, the filter sheet 52 may be secured to the frame member 54 by chemical, physical or mechanical means. That is, an adhesive may be employed or a heat sealing process may be used to secure the filter sheet to a portion of the frame member, such as a single rim portion 58 or 56, illustrated in FIGS. 5 and 6, respectively. Alternatively, the filter sheet may be sandwiched between two parts of a frame member, as illustrated in FIGS. 4 and 9. That is, upper and lower rim portions 56 and 58, respectively, may be secured to the peripheral edges of the filter sheet 52 or to one another with the peripheral edge of the filter sheet lying therebetween. This may be accomplished by heat sealing, adhesively securing, crimping, stapling or the like. The filter sheet is preferably secured to the frame member only at its peripheral edge. The peripheral edge of the filter sheet may contact the inwardly extending portion(s) of the frame member 56c and/or 58c, which are contiguous to substantially vertical wall portion(s) 56b and/or 58b or, as illustrated in FIGS. 4 to 9, the filter sheet may lie coextensive with the entire edge or rim portions of the substantially "Z" configured frame member 56a, 56b, 56c and/or correspondingly shaped 58a, 58b, 58c.

Figure 3A:
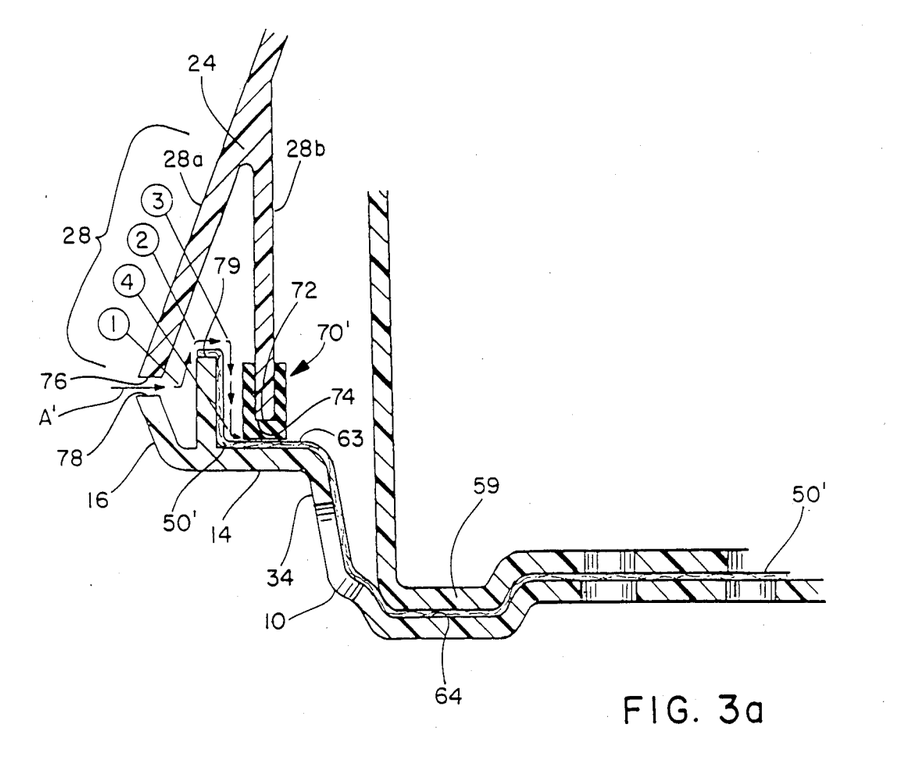
FIG. 3a is a partial sectional view similar to FIG. 3 of an alternative embodiment of the sterilization container, filter element and instrument tray according to the present invention.
Figure 3B:
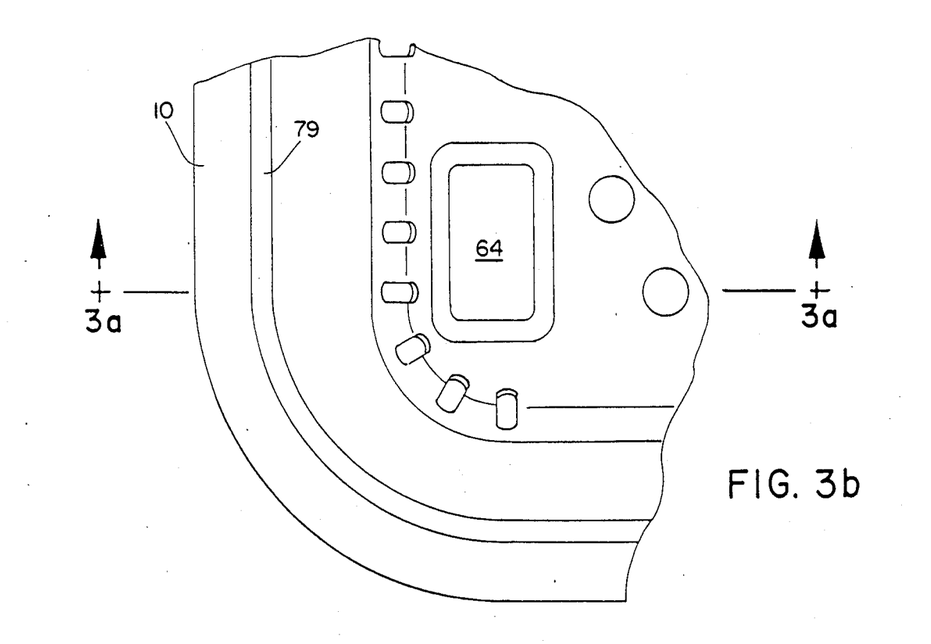
Figure 10:
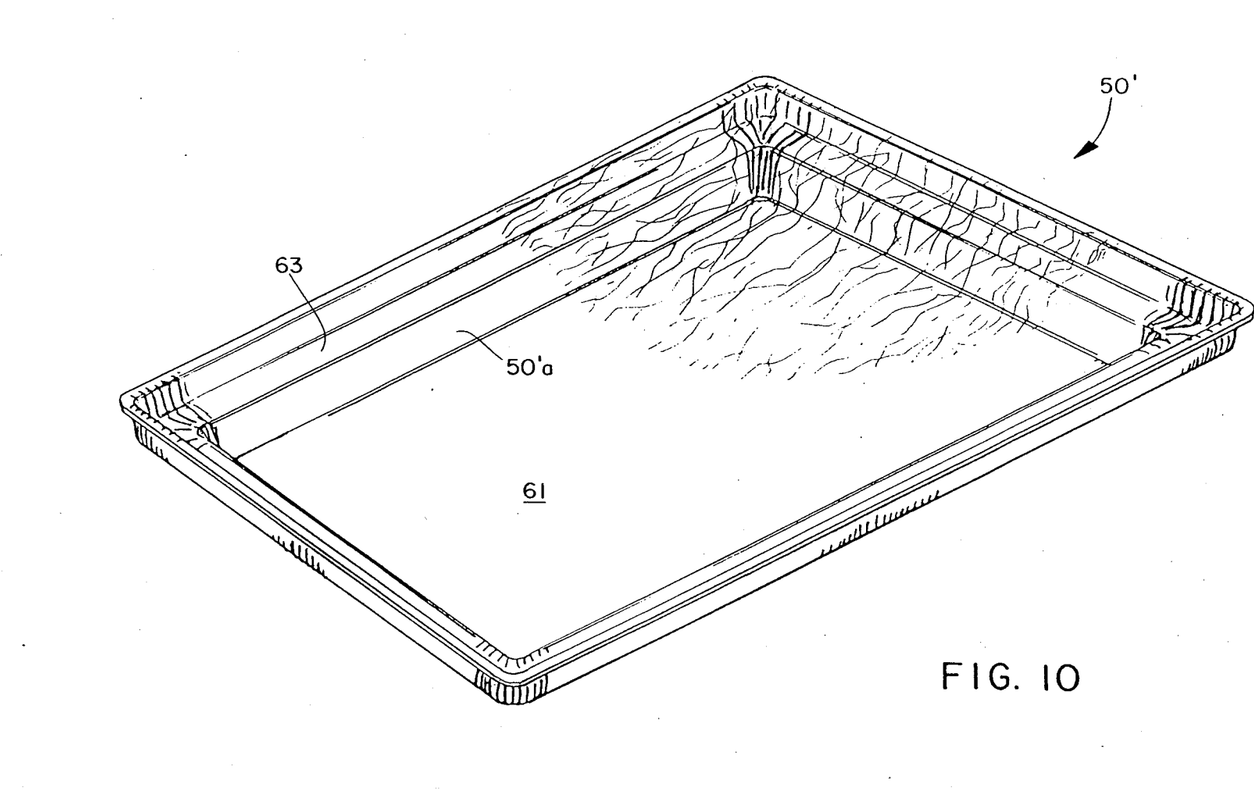

According to the invention, the filter element 50' (FIGS. 3a and 10) may have the alternate construction of a filter sheet with no hard frame, shaped by molding or pressing a flat sheet into a three dimensional unitary configuration, as shown in FIG. 10, to conform to and fit inside the container base member, as shown in FIG. 3a. As shown, the sides 50a' of the filter element 50' extend vertically from the flat bottom 61 and are folded at the corners and pressed to a smoothly curved shape nesting exactly within the base member with a peripheral rim portion 63 extending laterally under the gasket 70 between the cover and base member. In all the embodiments, the filter sheet 52 is preferably formed from a material which is thermally stable at temperatures employed for steam sterilization if that is the method to be employed to effect sterilization. The material from which the filter sheet is formed should also be chemically inert and insoluble in materials employed as chemical sterilants, such as ethylene oxide. The material must also permit passage of sterilizing fluids while excluding passage of microorganisms. Thus, the material should have an absolute pore rating or provide a throughpath of less than one-half micron, the size of the smallest known bacteria. Materials preferred for use as the filter sheet may include nonwoven mats of microfibers of thermoplastic polymers such as polyethylene and particularly polypropylene. Preferred materials include 10 to 20 mil in thickness nonwoven, fabric-like mats of generally discontinuous, thermoplastic polymeric microfibers or laminates thereof of the type described in U.S. Pat. No. 4,041,203.

As seen in FIG. 3a, when the filter element 50' is a soft, shaped element with no hard frame, the locating ribs (e.g., 66, FIG. 1) are eliminated and the filter element is located by nesting in the container base member. For locating the tray 34, cooperating means are provided on the base member and the tray, herein shown as projecting feet 59 which extend into depressions 64 in the bottom of the container base member at each corner, and the filter element 50' then extends into and lies against the bottom of these depressions.

In the form of filter element according to the present invention which includes the frame member 54 which is preferably rigid or inflexible, that is, self-supporting, the frame member is commensurate in shape to the container base member in which it is placed. When made according to the alternative embodiment of FIGS. 3a and 10, the filter element 50' is desirably constructed of solely filter material and is shaped to a three dimensional form which has sufficient structural integrity to retain its shape while being handled, both before assembly and during assembly in the container base member.

Figure 7:
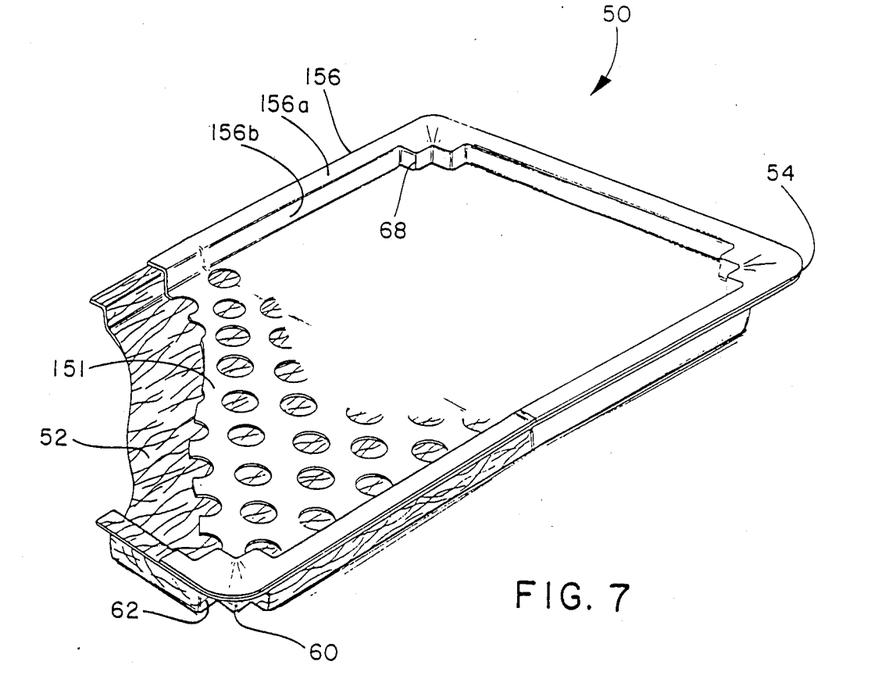
FIG. 7 is a perspective view of another embodiment of the filter element according to the present invention.
Figure 8:
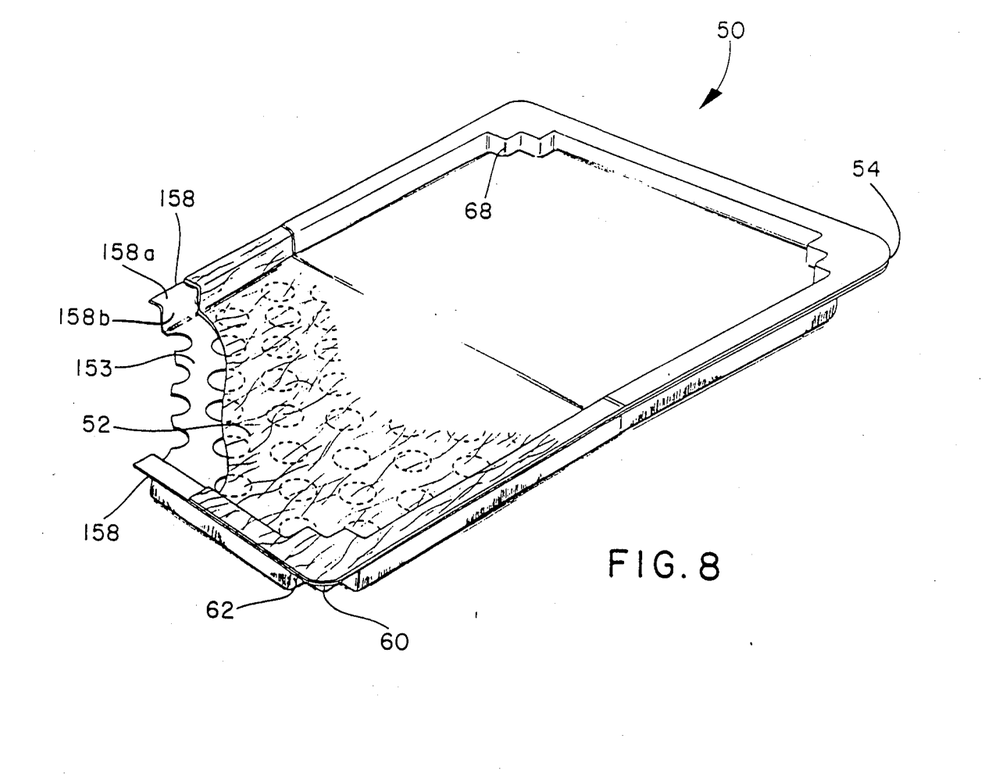
FIG. 8 shows in a perspective view another embodiment of the filter element according to the present invention.

Although FIGS. 4 to 6 illustrate embodiments of the filter element in which the filter sheet is secured to a peripheral rim, the present invention also contemplates a filter element having a frame member which includes a perforated portion extending substantially coextensive with the filter sheet. Such embodiments are shown in FIGS. 1, 3, and 7 to 9. The perforated portion 151 may be placed above the filter sheet 52, as illustrated in FIG. 7, so as to be located adjacent the lower portion of the removable tray when the sterilization and storage container of the present invention is fully assembled. Alternatively, the filter element may be provided with a perforated portion 153 located below the filter sheet 52 (FIG. 8) so that the perforated portion 153 is positioned adjacent the bottom of the container base member when the sterilization and storage container is fully assembled. The preferred embodiment shown in FIGS. 1, 3 and 9 has the filter sheet 52 secured between two coextensive perforated portions 151 and 153.

In the above-described preferred embodiment, the perforated portions 151 and 153 may be formed as separate members which may be secured to the corresponding rim portions 156 and 158, respectively, of the frame members. Preferably, however, each upper and lower frame member is formed of unitary construction composed of a rim and perforated portion.

The perforated portions of the frame member serve several functions. Although the preferred filter sheet material resists abrasion, a perforated covering reduces the potential for snagging, tearing, puncturing or otherwise damaging the filter material when it is being handled and while it is being assembled in the container. Once the filter element is positioned in the container base member, the container protects the filter sheet from being damaged by contact with an outside object. Thus, with both the framed filter elements of FIG. 3 and the soft filter elements of FIG. 3a, the container protects the filter sheet once assembled.

Figure 15:
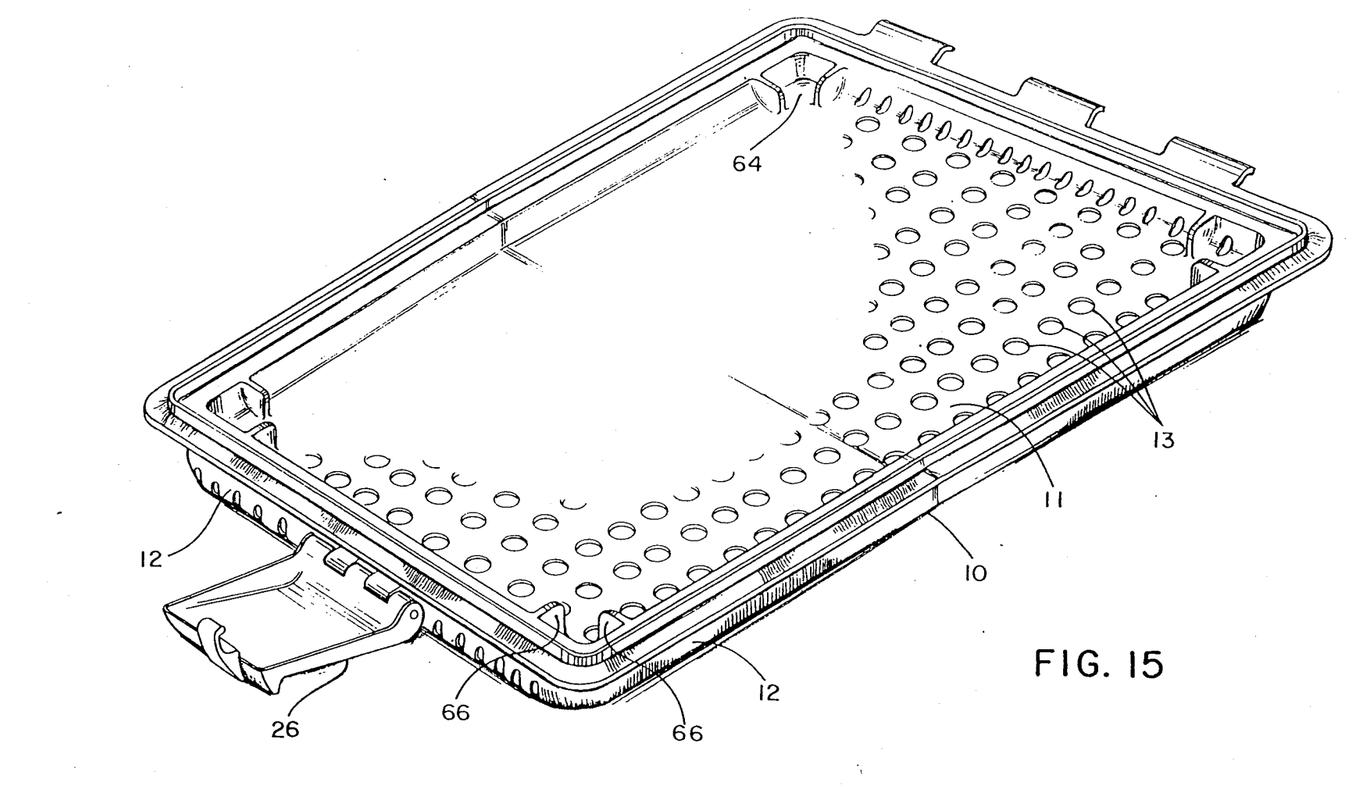
FIG. 15 illustrates in perspective an embodiment of the container base member according to the present invention.

The perforated portions also provide the frame member with additional rigidity and contribute to the overall configuration of the frame member which is commensurate in shape to the container base member. In order to position the filter element within the container base member so that it is properly secured therein when the container is closed, providing thereby an effective barrier to microorganism entry to the interior chamber of the sterilization and storage container, the frame member of the filter element is provided with a means for locating the filter element within the container. Preferably the filter element is positioned so that the frame member is in contact with some portion of the walls of the interior chamber. As the locating means, the filter element may be provided with projections or protrusions 60 and/or recesses 62. The projections may also be shaped to serve as feet which rest on the bottom of the container base member and provide both a means of locating the filter element within the container as well as providing a spaced relationship between the bottom surface of the perforated portion 153 and the inner surface of the container bottom 11. The projections 60 preferably engage complementary, corresponding recesses 64 in the container base member bottom or wall portion. In addition, or alternatively, the filter element may be provided with slots, recesses or indentations 62 which engage complementary, corresponding projections 66 (FIG. 15) on the bottom or wall portion of the container base member. The above-described projections may be individual localized protrusions or may be formed as a bead or beads on the wall or substantially vertical portion of the rim (58b or 158b), on the perforated portion 153 of the frame member, or on the inner surface of the side wall 12 or bottom 11 of the container base member. The corresponding recesses may be formed as engaging grooves in the container base member or frame member.

Materials suitable for use as the frame members should be inert to those materials commonly used as sterilizing agents and should resist the elevated temperatures used in heat sterilization, such as those encountered in autoclaves. Preferred materials include thin-gauge sheet steel and aluminum and polymeric materials, such as polyethylene and polypropylene of suitable molecular weights.

In addition to including a means of locating the filter element within the interior chamber of the sterilization container, the present invention may also include a means of locating the removable tray 30 in the interior chamber of the sterilization container. As shown in FIGS. 1 and 4 to 9, this preferably includes at least one recess in at least one of the tray and the frame member of the filter element and at least one corresponding projection or recess engaging portion on the other of the removable tray 30 and the frame member of the filter element. These recesses and projections or recess engaging portions may be of the same type as described above as the means for locating the filter element within the interior chamber of the sterilization and storage container.

Another embodiment of the present invention incorporates both of the above-described locating means in combination with means for locating the filter element within the interior chamber of the sterilization container and a means for locating the removable tray within the interior chamber. One way of accomplishing this is shown in FIGS. 1 and 4 to 9, in which an impression is made in the filter element such that at least one recess (as, for example, 62 exists in the outer surface of one of the frame members, preferably a rim portion, such as 56, 58, 156, 158, which impression also forms at least one projection such as 68 on the opposite side of the frame member or coextending frame member. The recess and projection engage projections or projecting portions and recesses, respectively, on the container base member and the lower portion of the removable tray. The impression, and the corresponding projection and recess, may be made in the filter element such that the orientation of the projection and recess are opposite that shown in the figures. In such a case, the placement and orientation of corresponding projections or projecting portions and recesses on the container base member and removable tray will be reversed.

The present invention is concerned not only with a container which is suitable for holding surgical instruments and materials during a sterilization process but also with such a container which will maintain an aseptic environment within the interior of the container after sterilization is completed and until such time as the container is opened. It is contemplated that the container may be used to deliver the instruments in aseptic condition to a place, such as an operating room, where the instruments are to be used. When the cover is removed, the instruments are presented in sterile condition to operating room personnel.

Several features of the present invention attain these objectives. When the container cover 20 is placed on the container base member 10 and lowered to a closed position, an interior chamber is defined therebetween communicating to the outside of the container through apertures 13 passing through the bottom and side walls of the container base member. The apertures 13 thus allow free passage of air, sterilizing fluid, particulate matter, as well as microorganisms to the interior of the container. However, when a filter element 50 or 50' is located within the sterilization container above the apertures 13, as, for example, in FIGS. 3 or 3a, communication between the interior chamber and the outside of the container is restricted to the passage of air and sterilizing fluids, such as steam, ethylene oxide, etcetera, but not to particulate matter or microorganisms. Thus, filter element 50 or 50', properly located within and sealed against the walls of the interior chamber, serves as a barrier to microorganisms. Furthermore, once sterilization is complete, the container cover 20 and filter element 50 define therebetween an aseptic region which is maintained until the cover is raised from the base member.

To assure the integrity of the aseptic region, a sealing means or gasket 70 is placed intermediate the container cover and the base member. The purpose of the gasket is to exclude microorganisms from the interior chamber at the juncture of the container cover and container base member. In all embodiments disclosed herein, the removable filter element has a peripheral portion extending to the exterior of the gasket 70. In the embodiment illustrated in FIG. 3, the gasket 70 sealingly contacts a surface of the rim portion of the frame member 54. As shown in the FIG. 3, the gasket 70 is located between a wall portion 24 of the container cover 20 and the upper surface of a rim portion 156a of the frame member. When the container cover is placed on the base member and tightly closed with clamping means 26, gasket 70, which should be compressible and preferably resilient, further serves to even out the pressure on the surface of the frame member which it contacts as well as between the contacting surfaces of the frame member and the container base member which are sealed against each other.

The gasket may be formed from any material which is thermally and chemically resistant to the conditions commonly employed in sterilization procedures. It may be affixed to either the container cover or, in another embodiment, the base member, but is, in the preferred embodiment illustrated in FIG. 3, affixed by a tongue and groove arrangement to the inner wall 28b of the double wall portion 28 of the container cover.

In the embodiment of the invention shown in FIG. 3a, the gasket 70' engages a filter sheet 50' which is clamped between the gasket 70' and the lateral flange 14 of the container base member. When the container cover is tightly closed with the clamping means 26, the gasket 70' forms a seal with the flange 14. However, the integrity of the aseptic region is not solely dependent on the seal.

According to the invention, in all embodiments, a further means is provided for excluding bacteria from the interior aseptic region of the sterilization container of the present invention. Specifically, a construction and arrangement is provided to serve as what is termed a "Pasteur Probability Filter" which is based on experiments conducted by the famous chemist, biochemist and microbiologist. Pasteur's experiments indicated that a tortuous pathway is effective in obstructing microorganisms when the pathway has a sufficient number of changes in direction. Thus, by providing a sufficiently tortuous or devious path, an additional microorganism barrier may be effected. The present invention contemplates such a probability filter by providing a tortuous path having four right angle turns from outside the container to the exterior of the sealing means on the base member and cover peripherally adjacent and exterior to the sealing means. In both constructions depicted in FIGS. 3 and 3a, the lower portion of the container cover wall 24 forms a bifurcated or double wall section 28, which includes an outer section 28a and a spaced apart inner section 28b. Gasket 70 is affixed to the depending edge of the inner wall 28b, the face 72 of the depending edge being in sealing contact with a surface of the groove 74 formed in the gasket 70 (FIG. 3) or in the gasket 70' (FIG. 3a). The outer wall portion 28a is constructed to be in close spaced relationship to an extension 16 of the outwardly projecting rim or flange portion 14 of the container base member. This space is provided to allow for proper sealing between the container cover and the base member by means of gasket 70. The lower end face 76 of the outer wall portion 28a is arranged substantially parallel to the upper surface 78 of the rim extension 16. Projecting upwardly and substantially at a right angle from rim 14 is a rail or rib 79. The rail is arranged intermediate the inner and outer wall sections 28a and 28b and in close proximity to the peripheral edge of the frame member 54 and gasket 70 but spaced so as to leave clearance between the gasket 70 and filter element 50' in the embodiment of FIG. 3a.

In the unlikely situation in which the gasket 70 were to lose its integrity and fail in its sealing capacity, thereby allowing a potential avenue of entry to the aseptic region within the interior chamber of the container, a microorganism entering the opening between surfaces 76 and 78 would still fail to enter the aseptic region by following the route designated by the dashed arrows A or A' (FIGS. 3 and 3a). Whereas three sharp turns are generally sufficient to serve as a microorganism barrier according to the principle of the Pasteur Probability Filter, path A or A', which the preferred structure of the present invention requires a microorganism to travel, is sufficient to stop microorganisms before they reach gasket 70 by requiring four turns, designated by the circled numbers in FIGS. 3 and 3a. Likewise, even loss of integrity of the gasket 70 sufficient to defeat sealing contact between the frame member and a wall of the container, such as between the lower surface of the rim 158a of the frame member and the upper surface of the container base member flange or rim portion 14 would still not provide access for a microorganism to the asceptic region after sterilization has been completed. Thus, those microorganisms entering apertures 13 and traveling the path indicated by dashed pathway B (FIG. 3) would be required to pass through at least three sharp turns in their tortuous path. Thus, both pathways A and B constitute paths which are sufficiently tortuous for a microorganism as to foreclose entry to the aseptic region of the container according to the Pasteur Probability Filter principle.

Figure 11:
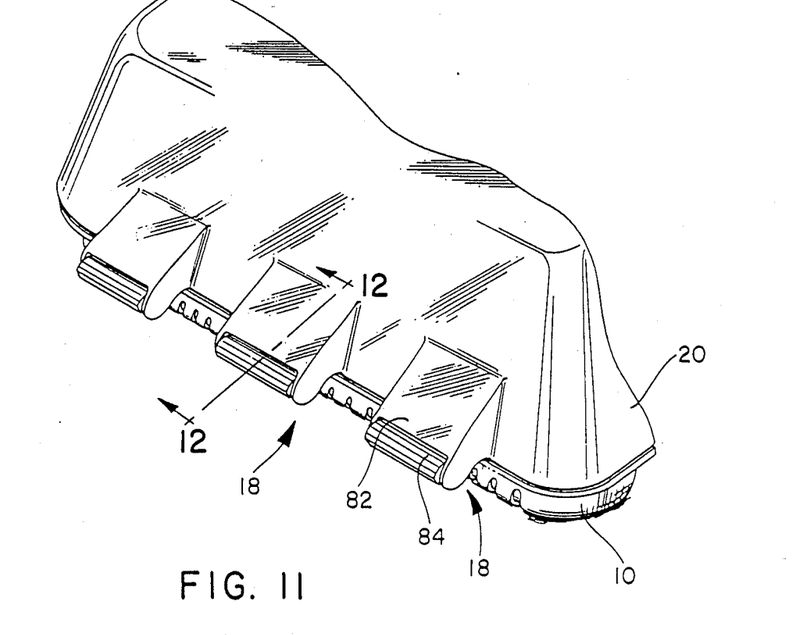
FIG. 11 shows a perspective view of an embodiment of a hinge which secures the container cover to the container base member.
Figure 12:
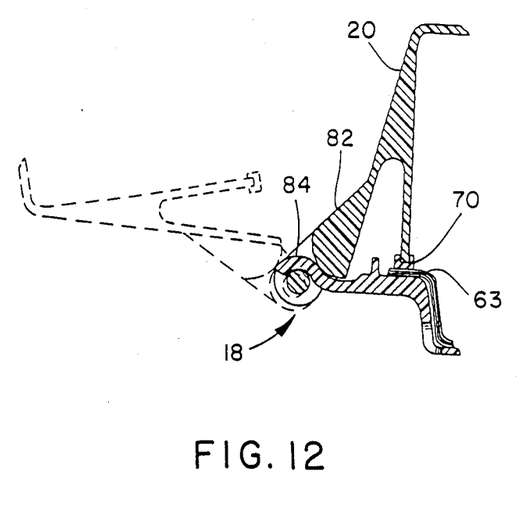
FIG. 12 illustrates, in section, the closed and, in phantom, the open positions of the hinge and a portion of the container cover, base member and filter element of the embodiment shown in FIG. 11 taken along line 12—12.

The hinge 18, illustrated in greater detail in FIGS. 11 and 12, is formed from two arcuate engaging members 82 and 84, which are secured to the container cover and base member, respectively. The hinge members 82 and 84 are so constructed that when the container and base member form an angle which exceeds approximately 90 degrees, the hinge members disengage and the container cover may be completely removed from the base member. Once separated from the base member, the cover may be used as a receptacle for contaminated instruments or materials.

Industrial Applicability

The present invention provides a lightweight combination sterilization and storage device for surgical instruments and materials which can be rapidly assembled and disassembled. The sterilization container assures maintenance of an aseptic condition of the interior of the device and the contents thereof after a suitable sterilization procedure.

I claim:

1. A container for sterilizing and storing instruments in sterilized condition comprising, in combination:

a container base member having a bottom with apertures and sidewalls extending upwardly from a periphery of said bottom of said container base member;

a container cover on said base member, said base member and cover together defining an interior chamber;

sealing means between said container cover and base member, said sealing means having an exterior portion disposed away from said interior chamber of said container;

a removable tray for instruments to be sterilized positioned within said interior chamber of said container;

means for locating said tray within said interior chamber of said container;

a removable filter element commensurate in shape to said container base member located in said interior chamber intermediate said bottom of said base member and said tray and having a peripheral portion extending to said exterior portion of said sealing means, whereby said sealing means forms a barrier to microorganisms between said container cover and said peripheral portion of said filter element;

said filter element and said apertures in said base member providing a filter path for sterilizing fluid from outside said container to an aseptically maintained region within said interior chamber; and means on said base member and cover peripherally adjacent and exterior to said sealing means providing a tortuous path from outside said container to the exterior of said sealing means so as to define a probability filter which serves as a barrier to passage of microorganisms through said tortuous path to said sealing means and limits access for microorganisms from outside said container to said interior chamber where instruments may remain after sterilizing through either said filter path which is obstructed by said filter element or said tortuous path which is obstructed by said probability filter and said sealing means.

2. The container of claim 1 wherein means are attached to said tray to maintain said tray and said filter element in spaced relationship.

3. The container of claim 2 wherein the bottom of said container base member declines from an intermediate portion towards its extremities, and the tray is provided with feet to maintain said spaced relationship.

4. The container of claim 1 wherein said means for locating said filter element comprises at least one projection provided on said filter element and at least one engaging recess for said projection formed in said container base member.

5. The container of claim 4 wherein said tray locating means is provided in said filter element.

6. The container of claim 5 wherein said tray locating means comprises at least one projection provided on said removable tray.

7. The container of claim 5 wherein said tray locating means comprises at least one recess provided in said removable tray and at least one recess engaging portion on said filter element.

8. The container of claim 5 wherein said tray locating means comprises at least one recess provided in said container base member, at least one recess engaging portion on said removable tray, and both at least one projection and at least one engaging recess provided on said filter element for inter-engagement with said at least one recess and said at least one recess engaging portion, respectively.

9. The container of claim 5 wherein said tray locating means comprises at least one projection provided on said filter element.

10. The container of claim 5 wherein said tray locating means comprises at least one recess provided in said filter element and at least one recess engaging portion on said removable tray.

11. The container of claim 5 wherein said tray locating means comprises at least one recess provided in said removable tray, at least one recess engaging portion on said container base member, and both at least one projection and at least one engaging recess provided on said filter element for inter-engagement with said at least one recess and said at least one recess engaging portion, respectively.

12. The container of claim 1 wherein said tray has a cover and said container cover and tray cover are formed from a transparent plastic material.

13. The container of claim 1 wherein said filter element is self-supporting and comprises a frame member including a rim portion and a pair of perforated portions, and a filter sheet, the periphery of such filter sheet being secured to said rim portion, said filter sheet being arranged intermediate and in substantially coextensive relationship with said perforated portions of said frame member.

14. The container of claim 1 wherein the height of said container cover is greater than said base member.

15. The container of claim 1 wherein said filter element comprises a filter sheet and a filter frame member defining said peripheral portion of said filter element.

16. The container of claim 1 wherein said filter element comprises a material including a mat of microfibers formed into a three-dimensional liner which nests within said container base member.

17. The container of claim 1 wherein said filter element is self-supporting and comprises a frame member and a sheet of filter material, said filter material including a laminated mat of microfibers and nonwoven web.

18. The container of claim 1 wherein said means for locating said filter element comprises at least one projection provided on said container base member and at least one engaging recess for said projection formed in said filter element.

* * * * *